Figure 1:
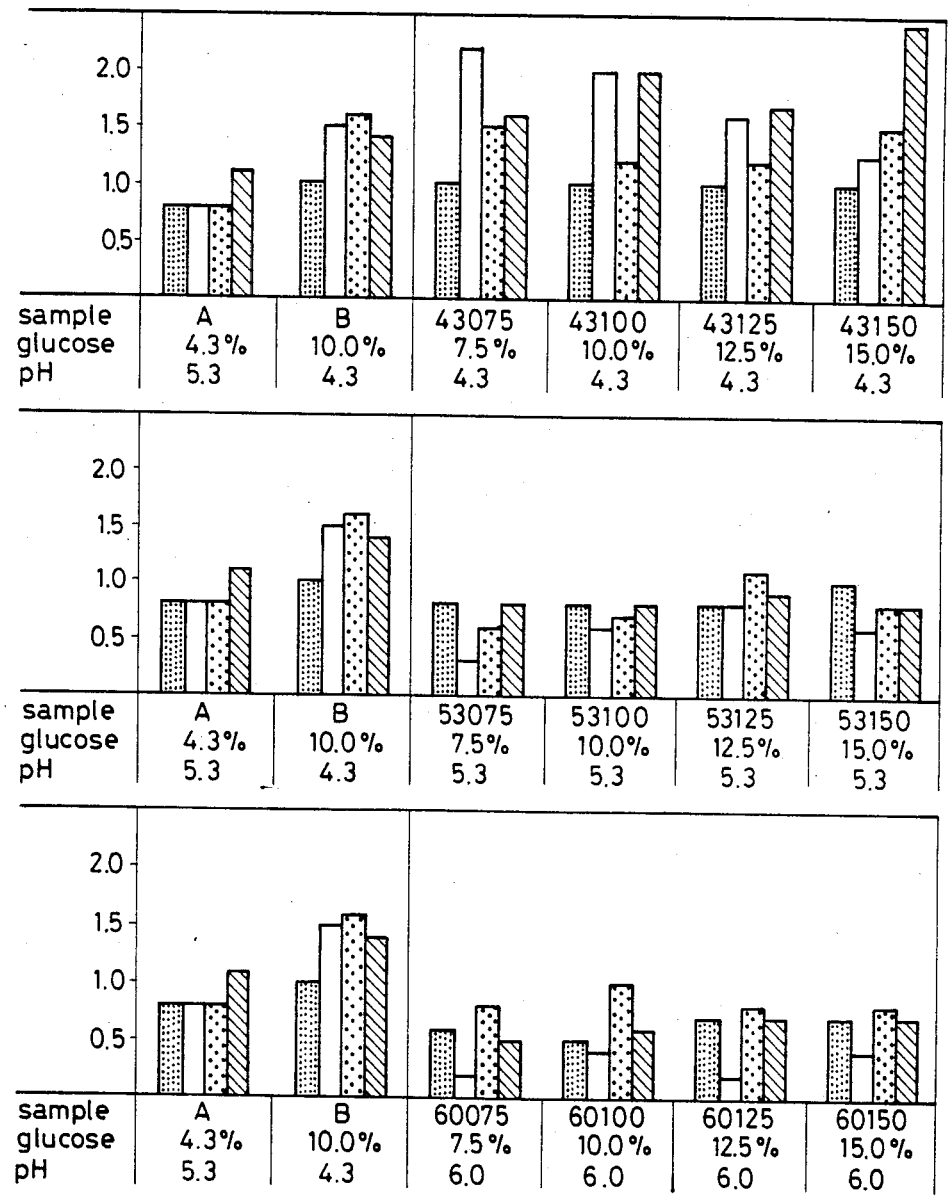

United States Patent [19]

Sugiyama et al.

[11] Patent Number: 4,576,930

[45] Date of Patent: Mar. 18, 1986

[54] TRANSFUSION PREPARATION FOR INTRAVENOUS INFUSION

[75] Inventors: Tohru Sugiyama; Yasuo Suzuki; Katsumasa Katagiri, all of Shimizu; Satoshi Furutani, Yaizu, all of Japan

[73] Assignee: Shimizu Pharmaceutical Co., Ltd., Shimizu, Japan

[21] Appl. No.: 511,494

[22] Filed: Jul. 7, 1983

[30] Foreign Application Priority Data

Jul. 20, 1982 [JP] Japan .................................. 57-127215

[51] Int. Cl.$^4$ ............................................. A61K 31/70
[52] U.S. Cl. ...................................... 514/23; 536/117; 536/17.1; 536/121
[58] Field of Search ......................... 536/1.1; 424/180; 514/23

[56] References Cited

U.S. PATENT DOCUMENTS

| | | | |
|---|---|---|---|
| 3,928,135 | 12/1975 | Milner | 424/180 |
| 4,021,543 | 5/1977 | McKay | 424/180 |
| 4,182,756 | 1/1980 | Ramsay et al. | 424/180 |
| 4,322,407 | 3/1982 | Ko | 424/180 |
| 4,434,160 | 2/1984 | Jeretin et al. | 424/180 |

*Primary Examiner*—Johnnie R. Brown
*Attorney, Agent, or Firm*—Burgess, Ryan & Wayne

[57] ABSTRACT

A transfusion preparation for intravenous infusion which contains glucose, electrolytes, a chelating agent, e.g., citric acid, a salt of polyhydric alcohol or monosaccharide phosphoric ester, e.g., sodium glycerophosphate and has a pH adjusted to 5 to 7.5. This preparation is free from coloring or precipitation on autoclave sterilization and can be administered into the central and peripheral veins without affecting venous tissue.

7 Claims, 1 Drawing Figure

TRANSFUSION PREPARATION FOR INTRAVENOUS INFUSION

The present invention relates to a transfusion or infusion preparation for intravenous infusion.

Intravenous transfusion therapy, which is to be conducted in cases where per os or per tubam supplementation of water, electrolytes, nutrients and so on is difficult, is one of the important therapeutic means in the clinical field.

Intravenous transfusion therapy has a long history. It is based on the discovery of blood circulation by William Harvey in 1616. Since then, intravenous administration of water, electrolytes (including minerals), three primary nutrients, etc. has been attempted, and nowadays a variety of transfusion preparations are on the market. Transfusion preparations can roughly be classified into four categories: electrolyte transfusion preparations, nutritive transfusion preparations, osmotic transfusion preparations and blood preparations. The preparations on the market belong to one or more of these categories. These preparations are infused mainly through the peripheral vein. Generally, nutritive transfusion preparations are preferably hypertonic solutions containing nutrients at high concentrations for the purpose of supplying nutrients. However, such hypertonic solutions are liable to irritate the peripheral vessel wall to cause phlebitis, and therefore, 5% glucose solutions, which are isotonic, are used in most cases. The calorific value suppliable with such isotonic solutions cannot exceed 500-600 calories per day when the balance to water is taken into consideration. According to an accepted opinion, further supply of calories is difficult. Therefore, the method of administering hypertonic solutions containing glucose in an amount of 20% to 30% through the central vein has recently been adopted. However, in nutritive transfusion therapy by the central vein route, the procedure for the central vein catheterization is troublesome and, in addition, some problems are encountered in using the central vein as the transfusion route, such as (1) infection: septicemia, catheter infection; (2) thrombosis; (3) leakage of transfusion fluids and (4) complications accompanied by catheterization: pneumothorax, hemothorax, nerve injury, vascular injury, catheter embolus, air embolus, etc. On the other hand, fat emulsions, which are not high in osmotic pressure, are used in combination with glucose since the incidence of phlebitis is less frequent with them. However, in such a case, too, side effects such as liver damage, hyperlipemia or adverse effects on the circulatory and respiratory systems cannot be overlooked.

Such administration through the central vein demands well-controlled institutions and skilled persons, and accordingly a transfusion preparation capable of supplying nutrients through the peripheral blood vessel is desired.

On the other hand, glucose has conventionally been a main source of calories to be administered through the peripheral vein. Although glucose is the safest carbohydrate source, its neutral solution undergoes caramelization upon heating for sterilization, which leads to intensive coloration and formation of degradation products such as hydroxymethylfurfural. For preventing such a reaction, glucose solutions for injection are prepared under conditions as acidic as possible. By way of illustration, when the pH values of commercial glucose infusions were measured, infusions containing 5% of glucose showed pH values in the range of 4.5 to 4.8, those containing 10% of glucose showed pH values from 4.0 to 4.8, those containing 20% of glucose showed pH values from 3.8 to 4.6 and those containing 40% of glucose showed pH values from 3.6 to 4.5, and those containing 50% of glucose showed pH values from 3.5 to 4.2. Thus, all of these infusions showed pH values below pH 5.0 and the pH values were lower with increasing glucose concentrations. In the case of commercial preparations containing both glucose and electrolytes, the pH values of those containing 2 to 3% of glucose were less than 5.5 and those containing larger amounts of glucose showed pH values below 5.0.

However, the pH values of these preparations are far away from the physiological pH levels. Moreover, as a large amount of acid is added for pH adjustment, their titration acidities are increased and this is known to be a causative factor of thrombophlebitis.

Moreover, in transfusion therapy, an electrolyte balance is no less important than energy supply.

Of various electrolytes, phosphorus, calcium and magnesium are necessary for maintenance infusion but when phosphorus in a phosphate form is additionally included, there tends to develop a turbidity or precipitates of calcium phosphate or magnesium phosphate and this tendency is increased by heat sterilization to cause problems in the production of intravenous infusions.

To solve this problem, it could be contemplated to keep separate the phosphate ion from the calcium ion and mix them immediately before administration but such a procedure would not only be troublesome and time-consuming but also increase the likelihood of bacterial contamination.

Referring to an infusion containing both of the above-mentioned ions, the precipitation may be prevented by adjusting the pH of the infusion to a certain level. Such a procedure takes advantage of the known phenomenon that the equilibrium between two different calcium phosphates [$CaHPO_4$ and $Ca(H_2PO_4)_2$] is shifted toward the more soluble $Ca(H_2PO_4)_2$ side at lower pH values. However, it is difficult, by such a procedure, to increase the pH of the preparation beyond 5.0, generally the level of pH 4.7 being the limit.

To solve the above problems and provide a glucose-electrolyte infusion that would supply a sufficient energy and ensure an adequate electrolyte balance and which may be safely administered through the peripheral vein and be autoclave-sterilized without trouble, the present inventors conducted an intensive study. The study led to the following findings.

As mentioned above, administration of a hyperalimentation infusion with a hypertonicity or a high titration acidity into a peripheral vein tends to cause phlebitis. However, since the pH of glucose-containing infusions is confined to a narrow range on the acidic side, it has not been fully elucidated what cumulative effects are brought about on phlebitis by the pH, osmotic pressure and glucose concentration of an infusion.

Therefore, glucose-containing infusions having different compositions and pH values were prepared (Table 1) and administered into the peripheral vein to investigate their effects on phlebitis.

TABLE 1

| | | Na+ mEq/L | K+ mEq/L | Mg++ mEq/L | Ca++ mEq/L | Cl− mEq/L | Lactate ion L mEq/L | Lactate ion DL mEq/L | P mM/L | Glucose % | pH | Osmotic pressure mOsm/L |
|---|---|---|---|---|---|---|---|---|---|---|---|---|
| Control | A | 35 | 20 | — | — | 35 | | 20 | — | 4.3 | 5.3 | 349 |
| | B | 35 | 20 | 3 | — | 38 | | 20 | — | 10.0 | 4.3 | 670 |
| Samples | 43075 | 50 | 30 | 3 | 5 | 48 | 20 | | 10 | 7.5 | 4.3 | 633 |
| | 43100 | 50 | 30 | 3 | 5 | 48 | 20 | | 10 | 10.0 | 4.3 | 792 |
| | 43125 | 50 | 30 | 3 | 5 | 48 | 20 | | 10 | 12.5 | 4.3 | 964 |
| | 43150 | 50 | 30 | 3 | 5 | 48 | 20 | | 10 | 15.0 | 4.3 | 1148 |
| | 53075 | 50 | 30 | 3 | 5 | 48 | 20 | | 10 | 7.5 | 5.3 | 611 |
| | 53100 | 50 | 30 | 3 | 5 | 48 | 20 | | 10 | 10.0 | 5.3 | 778 |
| | 53125 | 50 | 30 | 3 | 5 | 48 | 20 | | 10 | 12.5 | 5.3 | 948 |
| | 53150 | 50 | 30 | 3 | 5 | 48 | 20 | | 10 | 15.0 | 5.3 | 1183 |
| | 60075 | 50 | 30 | 3 | 5 | 48 | 20 | | 10 | 7.5 | 6.0 | 601 |
| | 60100 | 50 | 30 | 3 | 5 | 48 | 20 | | 10 | 10.0 | 6.0 | 764 |
| | 60125 | 50 | 30 | 3 | 5 | 48 | 20 | | 10 | 12.5 | 6.0 | 929 |
| | 60150 | 50 | 30 | 3 | 5 | 48 | 20 | | 10 | 15.0 | 6.0 | 1139 |

Rabbits were used as test animals in 14 groups of 5 individuals, and each infusion was administered into the auricular vein through a stainless steel needle in the dose of 50 ml/kg/day over a period of 6 hours for a total of 5 days. Then, a tissue was collected at a position 1 cm away from the infusion site for a histological examination. The findings are shown in Table 2 and the average numerical evaluation scores are given in FIG. 1.

FIG. 1 is a graphic representation of the results, expressed in terms of mean numerical evaluation scores, of a dermatological examination of the tissue around the site of infusion in rabbits administered sample transfusion fluids into the auricular veing daily for 5 days.

TABLE 2

| Sample | No. | Endothelial damage | Thickening of wall | Cellular infiltration | Thrombus | Others |
|---|---|---|---|---|---|---|
| B | 1 | + | + | + | + | |
| | 2 | + | ++ | ++ | ++ | |
| | 3 | + | ++ | ++ | ++ | |
| | 4 | + | ++ | ++ | + | |
| | 5 | + | + | + | + | |
| | Average score | 1.0 | 1.5 | 1.6 | 1.4 | |
| 43075 | 1 | + | ++ | + | + | |
| | 2 | + | ++ | ++ | + | |
| | 3 | + | +++ | ++ | ++ | |
| | 4 | + | ++ | ++ | ++ | |
| | 5 | + | ++ | + | ++ | |
| | Average score | 1.0 | 2.2 | 1.5 | 1.6 | |
| 43100 | 1 | + | ++ | + | ++ | |
| | 2 | + | ++ | + | ++ | |
| | 3 | + | ++ | + | ++ | Necrosis |
| | 4 | + | ++ | ++ | ++ | |
| | 5 | + | ++ | ++ | ++ | |
| | Average score | 1.0 | 2.0 | 1.2 | 2.0 | |
| 43125 | 1 | + | ++ | ++ | ++ | Necrosis, edema* |
| | 2 | + | ++ | ++ | ++ | |
| | 3 | + | + | + | ++ | |
| | 4 | + | ++ | + | ++ | |
| | 5 | + | + | + | + | |
| | Average score | 1.0 | 1.6 | 1.2 | 1.7 | |
| 43150 | 1 | + | + | ++ | ++ | Edema, abscess* |
| | 2 | + | + | + | ++ | |
| | 3 | + | ++ | ++ | +++ | Necrosis |
| | 4 | + | + | ++ | ++ | |
| | 5 | + | + | + | +++ | |
| | Average score | 1.0 | 1.2 | 1.5 | 2.4 | |
| A | 1 | − | − | − | − | |
| | 2 | + | + | + | ++ | |
| | 3 | + | + | + | + | |
| | 4 | + | + | + | + | |
| | 5 | + | + | + | ++ | |
| | Average score | 0.8 | 0.8 | 0.8 | 1.1 | |
| 53075 | 1 | + | − | − | + | |
| | 2 | ± | − | − | + | |
| | 3 | + | ± | ++ | + | |
| | 4 | ± | − | ± | − | |
| | 5 | + | + | + | + | |
| | Average score | 0.8 | 0.3 | 0.6 | 0.8 | |
| 53100 | 1 | − | − | − | − | |
| | 2 | + | − | ± | + | |
| | 3 | + | + | + | ++ | |
| | 4 | + | + | + | + | |
| | 5 | + | + | + | + | |
| | Average score | 0.8 | 0.6 | 0.7 | 0.8 | |
| 53125 | 1 | − | − | − | − | |
| | 2 | + | + | + | + | |
| | 3 | + | + | ++ | ++ | |
| | 4 | + | + | + | + | |
| | 5 | + | + | ++ | + | |
| | Average score | 0.8 | 0.8 | 1.1 | 0.9 | |
| 53150 | 1 | + | + | + | + | |
| | 2 | + | − | ± | ± | |
| | 3 | + | + | + | + | |
| | 4 | + | − | ± | ± | |
| | 5 | + | + | + | + | |
| | Average score | 1.0 | 0.6 | 0.8 | 0.8 | |
| 60075 | 1 | − | − | + | − | |
| | 2 | ± | − | + | ± | |
| | 3 | ++ | + | ++ | ++ | |
| | 4 | − | − | − | − | |

TABLE 2-continued

|  |  |  |  |  |  |
|---|---|---|---|---|---|
|  | 5 | ± | — | — | — |
|  | Average score | 0.6 | 0.2 | 0.8 | 0.5 |
| 60100 | 1 | — | — | + | — |
|  | 2 | ± | — | + | ± |
|  | 3 | + | + | + | ++ |
|  | 4 | + | + | ++ | ± |
|  | 5 | — | — | — | — |
|  | Average score | 0.5 | 0.4 | 1.0 | 0.6 |
| 60125 | 1 | ± | — | + | ± |
|  | 2 | + | — | + | ± |
|  | 3 | ± | — | — | ± |
|  | 4 | ± | — | ± | ± |
|  | 5 | + | + | ++. | ++ |
|  | Average score | 0.7 | 0.2 | 0.8 | 0.7 |
| 60150 | 1 | + | ± | ± | + |
|  | 2 | + | ± | + | + |
|  | 3 | + | + | + | + |
|  | 4 | ± | — | + | ± |
|  | 5 | — | — | ± | — |
|  | Average score | 0.7 | 0.4 | 0.8 | 0.7 |

(Note)

| Legend | Evaluation | Score |
|---|---|---|
| — | No abnormality | 0 |
| ± | Very slight | 0.5 |
| + | Slight | 1.0 |
|  |  | 1.5 |
| ++ | Moderate | 2.0 |
| +++ |  | 2.5 |
| +++ | Severe | 3.0 |

*Skin findings

It will be apparent from Table 2 and FIG. 1 that the onset of thrombophlebitis is dictated primarily by pH rather than by the osmotic pressure and titration acidity of the infusion and that the severity of thrombophlebitis is greater at lower pH, with substantial inhibition being obtained as the pH approaches neutral.

While a pH level near neutral is desirable for infusions, the selection of such a pH level requires a solution of the problem of glucose caramelization during autoclave sterilization.

The test in which various reagents were added to a glucose-containing infusions revealed that the addition of a chelating agent is effective in suppressing the thermal discoloration and decomposition of glucose infusions having neutral or near-neutral pH values.

Moreover, the problem of calcium phosphate precipitation at neutral pH could be solved by using as a phosphorus source a phosphoric acid ester of a polyhydric alcohol or carbohydrate and the co-presence of said chelating agent is rather favorable to prevention of precipitation.

This invention has been accomplished on the basis of the above findings. This invention is directed to, in a transfusion preparation containing glucose and electrolytes, a preparation for intravenous infusion which comprises the preparation contains a non-toxic chelating agent and a pharmaceutically acceptable, water-soluble salt of a polyhydric alcohol or monosaccharide phosphoric ester as a source of phosphorous, with its pH adjusted to 5 to 7.5, preferably 5.6 to 7.5.

In this invention, the concentration of glucose may be selected from a broad range of, for example 5 to 40%, preferably 10 to 30% for administration via a central vein and 5 to 20% by way of a peripheral vein.

As said electrolytes, there may be employed the water soluble salts which are commonly employed for transfusions such as the hydrochlorides, acetates, etc. of metals such as sodium, potassium, calcium, magnesium and the like.

If desired, the so-called minerals such as zinc, iron, copper, iodine, manganese, etc. may be added in the form of water soluble salts.

The amounts of glucose and electrolytes in the present pharmaceutical preparation are preferably selected from the following ranges.

Glucose: 100–300 g/liter
Sodium: 0–120 mEq/liter
Potassium: 0–120 mEq/liter
Calcium: 0–20 mEq/liter
Magnesium: 0–20 mEq/liter
Chlorine: 0–200 mEq/liter
Phosphorus: 0–25 mEq/liter The above-mentioned non-toxic chelating agent is preferably a hydroxycarboxylic acid such as citric acid, salicylic acid, etc. or a polyaminocarboxylic acid such as ethylene diaminetetraacetic acid, although citric acid is most preferred, The chelating agent is used in the free form or, depending on cases, in the form of a salt.

The above-mentioned phosphorous is added in the form of a pharmaceutically acceptable, water-soluble salt of a polyhydric alcohol or saccharide phosphoric ester.

The phosphoric acid ester is exemplified by the phosphoric ester of such polyhydric alcohols as glycerine, mannitol, sorbitol, etc. and of such monosaccharides as glucose, fructose, etc., although salts of gycerophosphoric acid or glucose-6-phosphate such as the sodium and potassium salts are most desirable.

The above-mentioned compounds are dissolved in water and the solution is adjusted to pH 5 to ).5, preferably pH 5.6 to 7.5. The above-mentioned chelating agent may be used in this pH adjustment.

In the preferred embodiment of this invention, the following salts are used as electrolyte donors, while citric acid is used for pH adjustment.

Na: Sodium chloride, sodium lactate
K: Potassium chloride, potassium glycerophosphate
Ca: Calcium chloride
Mg: Magnesium chloride
P: Potassium glycerophosphate In the above-mentioned preferred embodiment, the pH of the preparation can be maintained within the range of 5.5 to 6.5 without causing discoloration due to carmelization of glucose or precipitation.

In contrast, when the glycerophosphate in the above formula is replaced with a differential inorganic phosphate such as potassium or sodium hydrogen phosphate, there occurs precipitation at pH levels over pH 4.5.

Therefore, the effect of this invention is obviously derived from the combined use of said phosphate ester as a phosphorus donor and said chelating agent.

Thus, the infusion according to this invention does not color on autoclave sterilization or undergo precipitation, thus being very stable. Moreover, since it does not materially affect the venous tissue in such a manner as to induce thrombophlebitis, it can be safely administered not only to the central vein but also to peripheral veins.

EXAMPLE 1

Glucose: 125 g
Potassium glycerophosphate: 2.483 g
KCl: 0.746 g
CaCl$_2$.2H$_2$O: 0.368 g
NaCl: 1.753 g
MgCl$_2$.6H$_2$O: 0.305 g
Sodium lactate: 2.241 g
Citric acid monohydrate: 0.350 g The above components were weighed and dissolved in distilled water for injection, followed by dilution with the same distilled water to make a total of 1000 ml (pH about 6.2). The dilution was adjusted to pH 6.0 with a small amount of lactic acid and, then, following the established manufacturing procedure for parenteral preparations according to the Japanese Pharmacopoeia, filtered, filled into ampoules, sealed, sterilized and tested.

As a result, the solution was found to meet the requirements imposed on parenteral preparations. The above injectable preparation was subjected to longterm storage stability testing. After storage at 40° C. 16 weeks, said preparation showed its excellent stability as compared with a control preparation produced in the same manner but without addition of citric acid (cf. Table 3 and Table 4).

TABLE 3

| (1) Absorption due to hydroxymethylfurfurals directly after sterilization | | | | |
|---|---|---|---|---|
| | | | | Absorbance at 284 nm |
| (1) With citric acid | | | | 0.119 |
| (2) Control | | | | 0.220 |
| (2) Extent of coloration directly after sterilization (in NBS units) | | | | |
| | L | a | b | ΔE$_1$* |
| (1) With citric acid | 100.0 | 0.0 | 0.2 | 0.2 |
| (2) Control | 99.0 | −0.0 | 0.7 | 0.7 |
| | ΔL | Δa | Δb | ΔE$_2$** |
| (2) − (1) | −0.1 | 0 | 0.5 | 0.5 |

*Difference in color from water;
**Difference in color between (2) and (1).
Remarks: The absorbance at 284 nm, which is an index to the extent of degradation of glucose, was smaller by about 50% than that of the control. In spite of the higher pH of the solution (5.93), the difference in color from water was as slight as 0.2NBS unit and thus indicated a slighter degree of coloration. As an injection, the preparation met the requirements in all the other qualitative tests (foreign matter test, etc.).

TABLE 4

| Results of 16-week storage stability testing at 40° C. | | | | |
|---|---|---|---|---|
| (1) Absorption due to hydroxymethylfurfurals (resulting from decomposition of glucose) | | | | |
| | | | | Absorbance at 284 nm |
| (1) With citric acid | | | | 0.260 |
| (2) Control | | | | 0.804 |
| (2) Extent of coloration (in NBS units) | | | | |
| | L | a | b | ΔE$_1$* |
| (1) With citric acid | 100.0 | −0.0 | 0.9 | 0.9 |
| (2) Control | 99.2 | −0.5 | 4.7 | 4.7 |
| | ΔL | Δa | Δb | ΔE$_2$** |
| (2) − (1) | −0.08 | −0.5 | 3.8 | 3.8 |

*Difference in color from water;
**Difference in color between (2) and (1).
Remarks: The preparation according to the invention which contained glucose in a concentration of 12.5% was satisfactorily stable in the above storage test conducted at 40° C. for 16 weeks. The coloration was slight (in NBS units: 0.5–1.5) ascompared with water, whereas the control was colored to an appreciable extent (in NBS units: 3.6–6.0).

EXAMPLE 2

Glucose: 125 g
Potassium glycerophosphate: 2.483 g
KCl: 0.746 g
CaCl$_2$.2H$_2$O: 0.368 g
NaCl: 1.753 g
MgCl$_2$.6H$_2$O: 0.305 g
Sodium lactate: 2.241 g
Citric acid monohydrate: 0.350 g The above components were weighed and dissolved in distilled water for injection, followed by dilution with the same distilled water to make a total of 1000 ml (pH about 6.2). Without pH adjustment, the dilution was treated in the same manner as in Example 1 and then tested.

As a result, the preparation thus obtained was qualified as an injection without doubt.

EXAMPLE 3

Glucose: 50 g
Potassium glycerophosphate: 2.483 g
KCl: 0.746 g
CaCl$_2$.2H$_2$O: 0.368 g
NaCl: 1.753 g
MgCl$_2$.6H$_2$O: 0.305 g
Sodium lactate: 1.681 g
Trisodium citrate dihydrate: 0.491 g The above components were weighed and dissolved in distilled water for injection, followed by dilution with the same distilled water to make a total of 1000 ml (pH about 8.0). The dilution was adjusted to pH 6.5 with a slight amount of lactic acid and then treated in the same manner as in Example 1 following the manufacturing procedure for parenteral preparations according to the Japanese Pharmacopeia. After pressure steam sterilization, the preparation was tested and found to have qualities for an injection.

EXAMPLE 4

Glucose: 300 g
Potassium glycerophosphate: 4.965 g
Calcium lactate pentahydrate: 2.004 g
Potassium lactate: 1.666 g
Magnesium acetate tetrahydrate: 0.751 g
NaCl: 0.409 g
Citric acid monohydrate: 0.350 g
Zinc chloride: 0.003 g The above components were weighed and dissolved in distilled water for injection, followed by dilution with the same distilled water to make a total of 1000 ml (pH about 6.6). The dilution was adjusted to pH 6.0 with a small amount of lactic acid and then treated following the manufacturing procedure for parenteral preparations according to the Japanese Pharmacopeia. After pressure steam sterilization, the parenteral preparation obtained was tested and, as a result, qualified as an injection. A storage test conducted at 50° C. for 4.5 weeks for guaranteeing the stability of the above parenteral preparation demonstrated its good stability as compared with a control injection prepared in the same manner but without addition of citric acid (cf. Table 5 and Table 6).

TABLE 5

| (1) Absorption due to hydroxymethylfurfurals directly after sterilization | |
|---|---|
| | Absorbance at 284 nm |
| (1) With citric acid | 0.183 |
| (2) Control | 0.220 |

(2) Extent of coloration directly after sterilization

TABLE 5-continued (in NBS units)

| | L | a | b | $\Delta E_1$* |
|---|---|---|---|---|
| (1) With citric acid | 100.1 | −0.0 | 0.5 | 0.5 |
| (2) Control | 100.0 | −0.0 | 0.7 | 0.7 |
| | $\Delta L$ | $\Delta a$ | $\Delta b$ | $\Delta E_2$** |
| (2) − (1) | −0.1 | 0 | 0.2 | 0.2 |

*Difference in color from water;
**Difference in color between (2) and (1).
Remarks: The citric acid-containing preparation according to this invention was more stable against sterilization than the control.

TABLE 6

Results of 4.5-week storage stability testing at 50° C.

(1) Absorption due to the hydroxymethylfurfurals
(resulting from decomposition of glucose)

| | Absorbance at 284 nm |
|---|---|
| (1) With citric acid | 0.948 |
| (2) Control | 2.26 |

(2) Coloration (in NBS units)

| | L | a | b | $\Delta E_1$* |
|---|---|---|---|---|
| (1) With citric acid | 99.1 | −0.6 | 5.8 | 5.9 |
| (2) Control | 94.1 | −0.9 | 19.8 | 20.7 |
| | $\Delta L$ | $\Delta a$ | $\Delta b$ | $\Delta E_2$** |
| (2) − (1) | −5.0 | −0.3 | 14.0 | 14.9 |

*Difference in color from water;
**Difference in color between (2) and (1).
Remarks: Although it contained glucose in a concentration as high as 30%, the preparation according to the invention was colored only to an appreciable extent (in NBS units: 3.0–6.0) during the 4.5-week storage at 50° C. whereas the control assumed a yellow color, the extent of coloration being very much (in NBS units: 12.0 or more).

EXAMPLE 5

Glucose: 125 g
Potassium glycerophosphate: 2.483 g
KCl: 0.746 g
CaCl$_2$.2H$_2$O: 0.368 g
NaCl: 1.753 g
MgCl$_2$.6H$_2$O: 0.305 g
Sodium acetate: 1.641 g
Trisodium citrate dihydrate: 0.491 g The above components were weighed and dissolved in distilled water for injection, followed by dilution to make a total of 1000 ml (pH about 8.2). The dilution was adjusted to pH 6.0 with a small amount of acetic acid and then processed following the manufacturing procedure for parenteral preparations according to the Japanese Pharmacopeia.

Upon subsequent testing, the preparation was satisfactorily qualified as an injection.

EXAMPLES 6 AND 7

A parenteral preparation was prepared in the same manner as in Example 1 except that 3.724 g of dipotassium glucose-1-phosphate (Example 6) or 3.724 g of dipotassium glucose-6-phosphate (Example 7) was used in place of potassium glycerophosphate used in Example 1. The extent of coloration and decomposition of glucose was in the order of Example 7> Example 6> Example 1.

EXAMPLES 8 AND 9

A parenteral preparation was prepared in the same manner as in Example 1 except that 0.620 g of disodium ethylenediaminetetraacetate (EDTA.2Na.2H$_2$O) (Example 8) or 0.267 g of sodium salicylate (Example 9) was used in place of citric acid monohydrate used in Example 1. The difference in color from water was 0.3 NBS unit (Example 8) or 0.4 NBS unit (Example 9).

EXAMPLE 10

A parenteral preparation was prepared following the formulation of Example 3 except that the amount of glucose was increased to 175 g (from 50 g). The components were weighed and dissolved in distilled water for injection, followed by dilution with the same distilled water to make a total of 1000 ml (pH about 8.0). The dilution was adjusted to pH 7.5 with a slight amount of lactic acid and then processed following the manufacturing procedure according to the Japanese Pharmacopeia. After intermittent sterilization, the preparation was tested and found to be satisfactorily qualifiable as an injection.

EXAMPLE 11

Glucose: 125 g
Potassium glycerophosphate: 2.483 g
KCl: 0.746 g
NaCl: 1.753 g
MgCl$_2$.6H$_2$O: 0.305 g
Sodium lactate: 2.241 g
Citric acid monohydrate: 0.350 g The above components were weighed and dissolved in distilled water for injection, followed by dilution with the same distilled water to make a total of 1000 ml (pH about 6.3). The dilution was adjusted to pH 6.0 with a slight amount of lactic acid and then processed in the same manner as in Example 1 following the manufacturing procedure according to the Japanese Pharmacopeia. Upon testing, the preparation was qualified as an injection. The difference in color from water was 0.3 NBS unit, whereas it was 0.7 NBS unit for an injection for comparison as prepared in the same manner but without addition of citric acid.

EXAMPLE 12

Glucose: 225 g
Potassium glycerophosphate: 2.483 g
KCl: 0.746 g
CaCl$_2$.2H$_2$O: 0.368 g
NaCl: 1.753 g
MgCl$_2$.6H$_2$O: 0.305 g
Sodium lactate: 2.241 g
Trisodium citrate dihydrate: 0.491 g The above components were weighed and dissolved in distilled water for injection, followed by dilution with the same distilled water to make a total of 1000 ml (pH about 8.0). The dilution was adjusted to pH 5.5 with lactic acid and then processed as in Example 1 following the manufacturing procedure according to the Japanese Pharmacopeia. The preparation was fully qualified as an injection. The difference in color from water was 0.1 NBS unit while that for an injection for comparison as prepared in the same manner but without addition of trisodium citrate was 0.6 NBS unit.

We claim:

1. In a transfusion preparation containing glucose and electrolytes for intravenous infusion, the improvement comprising the preparation containing a salt of citric acid, salicylic acid, ethylenediaminetetraacetic acid or lactic acid as a chelating agent, and a pharmaceutically acceptable, water-soluble glycerophosphate, glucose-1-phosphate or glucose-6-phosphate as a phosphorous source, and having a pH of 5 to 7.5.

2. A preparation accrding to claim 1 wherein the chelating agent is citric acid.

3. A preparation according to claim 1 wherein the phosphorous source is a potassium or sodium salt of glycerophosphoric acid.

4. A preparation according to claim 1 wherein the phosphorous source is a potassium or sodium salt of glucose-6-phosphate.

5. A preparation according to claim 1 wherein the pH is 5.6 to 7.5.

6. A preparation according to claim 1 wherein the electrolytes contain at least phosphorus, calcium and magnesium.

7. A preparation according to claim 1 wherein the electrolytes contain 100 to 300 g per liter of glucose, not more than 20 mEq per liter of calcium and not more than 25 mEq per liter of phosphorus.

* * * * *